(12) United States Patent
Plecko et al.

(10) Patent No.: US 9,393,029 B2
(45) Date of Patent: Jul. 19, 2016

(54) REAMER AND DRILL GUIDING DEVICE

(75) Inventors: Michael Plecko, Graz (AT); Martin Felder, Bellach (CH); Andreas Sigrist, Solothurn (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1671 days.

(21) Appl. No.: 12/700,225

(22) Filed: Feb. 4, 2010

(65) Prior Publication Data

US 2010/0228253 A1    Sep. 9, 2010

Related U.S. Application Data

(60) Provisional application No. 61/150,090, filed on Feb. 5, 2009.

(51) Int. Cl.
| | |
|---|---|
| *A61B 17/58* | (2006.01) |
| *A61B 17/60* | (2006.01) |
| *A61F 2/00* | (2006.01) |
| *A61B 17/16* | (2006.01) |
| *A61B 17/17* | (2006.01) |

(52) U.S. Cl.
CPC ......... *A61B 17/1637* (2013.01); *A61B 17/1717* (2013.01)

(58) Field of Classification Search
CPC .................. A61B 17/1717; A61B 17/1637
USPC ....... 606/79, 80, 82, 86 R, 87–89, 95, 96, 98, 606/104
See application file for complete search history.

(56) References Cited

U.S. PATENT DOCUMENTS

| | | | | |
|---|---|---|---|---|
| 3,867,932 | A | * | 2/1975 | Huene .............................. 606/80 |
| 5,667,513 | A | * | 9/1997 | Torrie et al. .................... 606/104 |
| 7,661,957 | B2 | * | 2/2010 | Tanimura ....................... 433/173 |
| 2002/0099382 | A1 | | 7/2002 | Salazar et al. |
| 2002/0193802 | A1 | * | 12/2002 | Zdeblick et al. ................ 606/96 |
| 2006/0036254 | A1 | * | 2/2006 | Lim ................................ 606/86 |

FOREIGN PATENT DOCUMENTS

| | | |
|---|---|---|
| CH | 240542 | 12/1945 |
| JP | H0382478 | 4/1991 |
| JP | 2006/503671 | 2/2006 |

* cited by examiner

*Primary Examiner* — Kevin T Truong
*Assistant Examiner* — Si Ming Ku
(74) *Attorney, Agent, or Firm* — Fay Kaplun & Marcin, LLP

(57) ABSTRACT

A device for guiding a drilling tool to form an opening in a bone, includes a body extending from a distal end to a proximal end, the body including a lumen extending therethrough, the lumen being sized and shaped to slidably accommodate a guidewire therein and a plurality of arms extending proximally from the proximal end, the arms being disposed about the lumen with a gripping surface of each arm being spaced radially from an axis of the guide wire lumen by a distance corresponding to a thickness of a guidewire to be received therein, the gripping surfaces gripping the guidewire to maintain a portion thereof extending proximally of the lumen along the axis of the lumen.

8 Claims, 4 Drawing Sheets

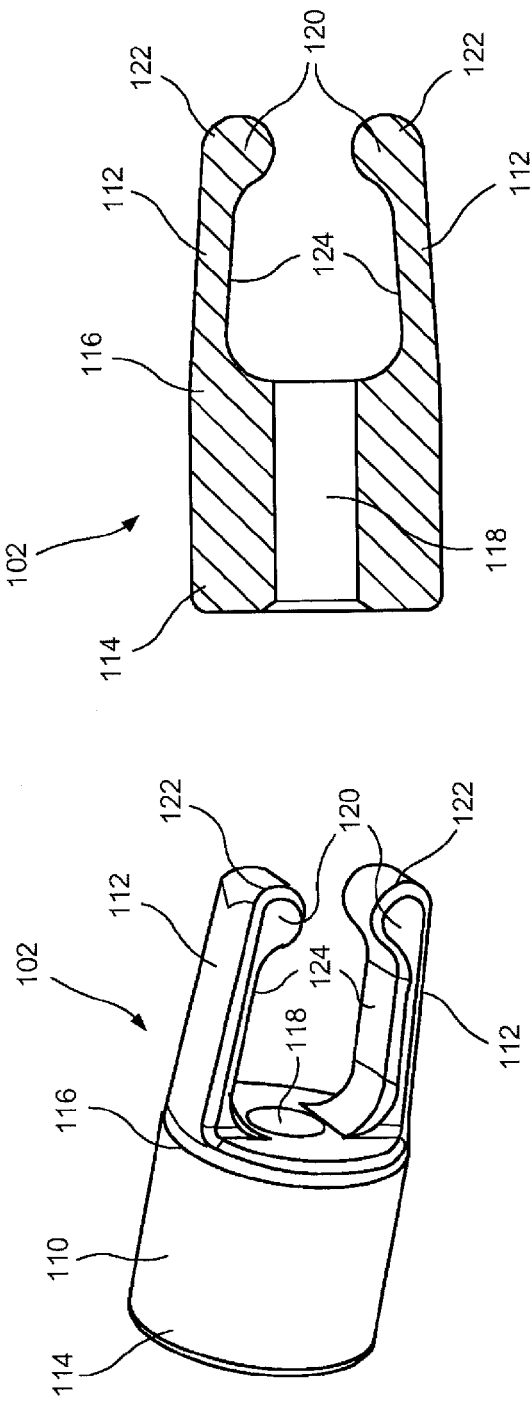
FIG. 2
FIG. 3
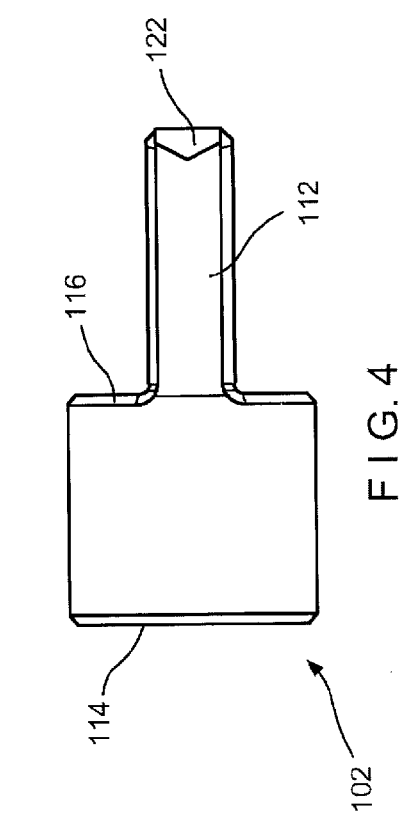
FIG. 4

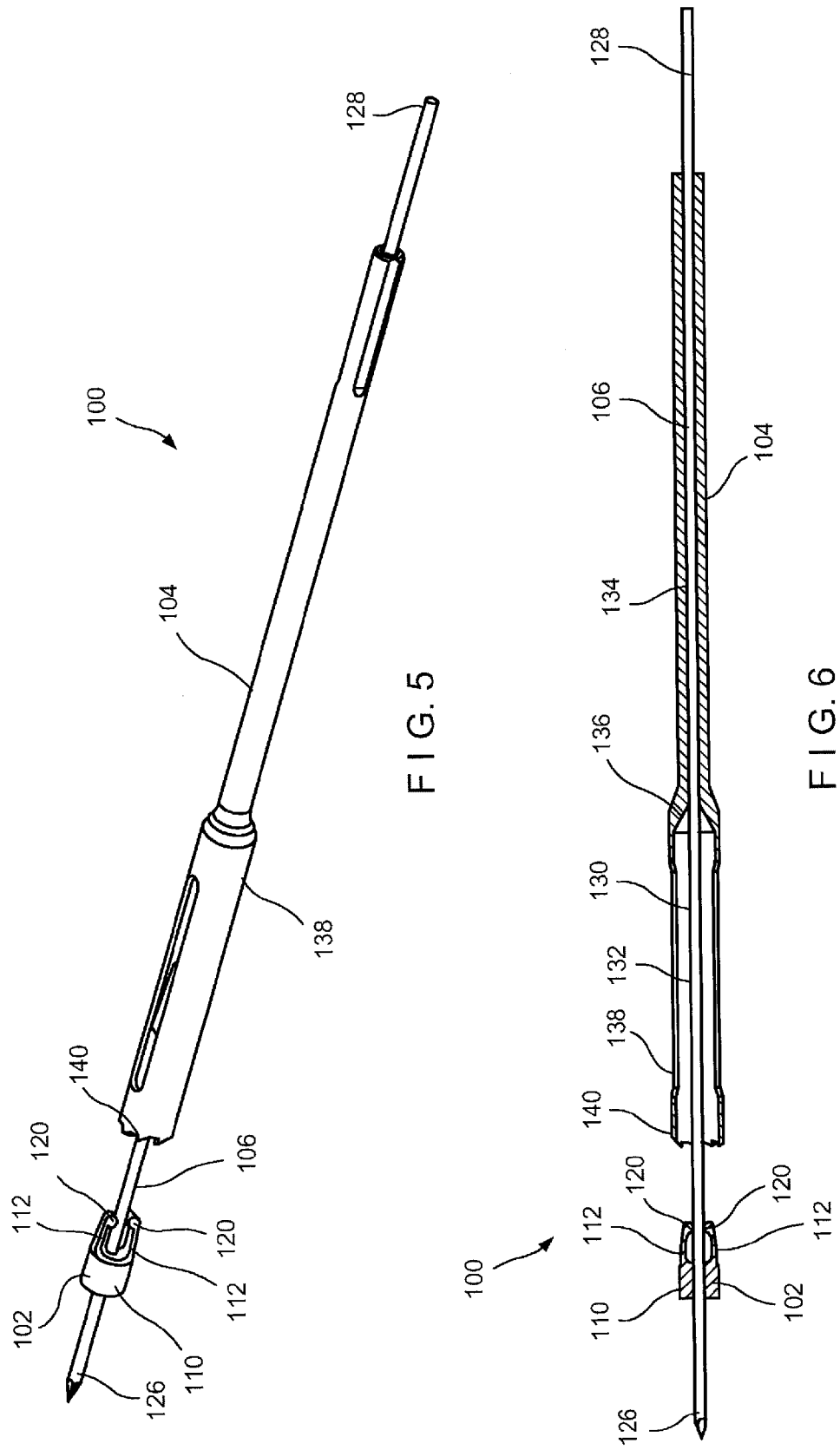

REAMER AND DRILL GUIDING DEVICE

PRIORITY CLAIM

The present application claims priority to U.S. Provisional Application Ser. No. 61/150,090 filed on Feb. 5, 2009 entitled "Reamer and Drill Guiding Device," the entire disclosure of which is incorporated herein by reference.

FIELD OF THE INVENTION

The present invention relates to devices for treating fractures and, in particular, relates to a device for guiding a drill or a reamer co-axially along a guidewire inserted into a bone such that an opening may be formed in the bone at a desired angle and position to accommodate the insertion of a fixation device therethrough.

BACKGROUND

An intramedullary nail is a device used to stabilize long bones such as the tibia or femur. The intramedullary nail is inserted into a medullary canal of the long bone to align and stabilize the bone after an opening through the cortical bone has been formed using, for example, a drill or reamer. To ensure a proper angle of insertion for the intramedullary nail, a guidewire (e.g., a k-wire) may be used to guide the drill or reamer into the bone at the desired angle. The guidewire is generally inserted into the bone at the desired angle and position and the drill or reamer is then slid over the guidewire. To attain the desired angle and position for the cortical bone opening, the drill or reamer should be co-axial with the guidewire. However, in some cases, a bending force at one end of the drill or reamer results in the drill or reamer becoming displaced such that the opening of the cortical bone is formed at an improper angle and/or position

SUMMARY OF THE INVENTION

The present invention is directed to a device for guiding a drilling tool to form an opening in a bone, comprising a body extending from a distal end to a proximal end, the body including a lumen extending therethrough, the lumen being sized and shaped to slidably accommodate a guidewire therein and a plurality of arms extending proximally from the proximal end, the arms being disposed about the lumen with a gripping surface of each arm being spaced radially from an axis of the guide wire lumen by a distance approximately corresponding to a thickness of a guidewire to be received therein, the gripping surfaces gripping the guidewire to maintain a portion thereof extending proximally of the lumen along the axis of the lumen.

BRIEF DESCRIPTION OF THE DRAWINGS

FIG. 2 shows a perspective view of a device according to the system of FIG. 1;

FIG. 3 shows a cross-sectional side view of the device of FIG. 2;

FIG. 4 shows another side view of the device of FIG. 2, rotated about a longitudinal axis thereof with respect to FIG. 3;

FIG. 5 shows a perspective view of the system of FIG. 1, in a guiding configuration;

FIG. 6 shows a cross-sectional side view of the system of FIG. 5;

DETAILED DESCRIPTION

The present invention, which may be further understood with reference to the following description and the appended drawings, relates to devices for treating fractures. In particular, exemplary embodiments of the present invention describe a device for guiding a drill or a reamer co-axially along a guidewire inserted into a bone such that an opening may be formed in the bone at a desired angle and position to accommodate the insertion of a fixation device therethrough. It will be understood by those of skill in the art that although the exemplary embodiments are described in regard to the formation of a cortical opening for the insertion of an intramedullary nail, the device may be used for creating a bone opening in any situation in which a guidewire is used. It should also be noted that the terms "proximal" and "distal," as used herein, are used to describe a direction toward (proximal) and away from (distal) a user of the device.

Figure 1:
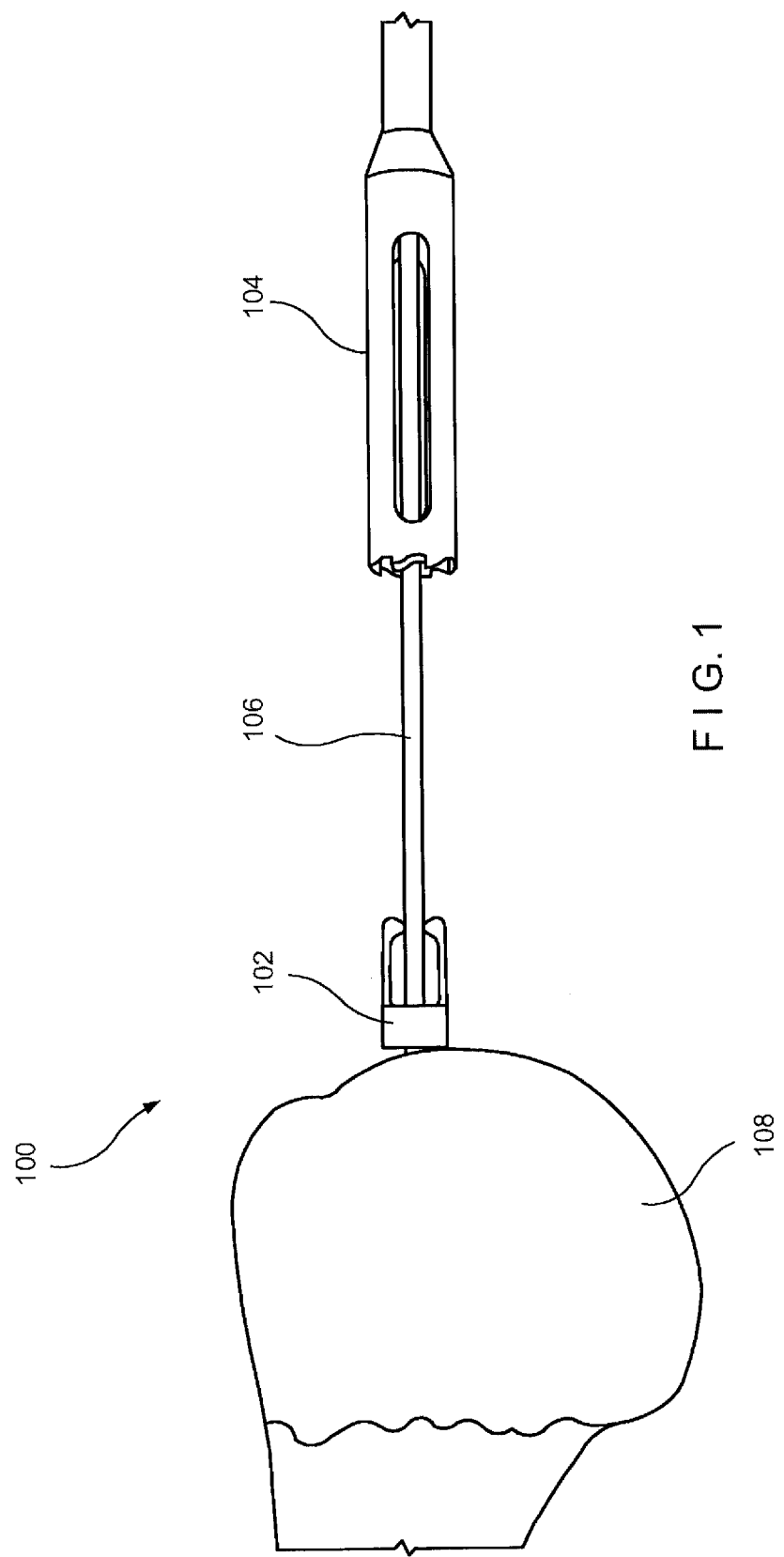
FIG. 1 shows a side view of a system according to an exemplary embodiment of the present invention.

As shown in FIG. 1, a system 100 according to an exemplary embodiment of the present invention comprises a device 102 that may be used to guide a drilling tool 104 co-axially along a guidewire 106 inserted into a bone 108 to form a cortical opening in the bone 108 at a desired angle and/or position. As shown in FIGS. 2-4, the device 102 comprises a body portion 110 and a plurality of arms 112. The body portion 110 extends longitudinally from a distal end 114 to a proximal end 116 and includes a lumen 118 extending therethrough from the distal end 114 to the proximal end 116. The lumen 118 is preferably sized and shaped to slidably accommodate the guidewire 106. In a preferred embodiment, the body portion 110 may be substantially cylindrical. However, it will be understood by those of skill in the art that the body portion 110 may take a variety of shapes and sizes.

The arms 112 extend from the proximal end 116 and are positioned around the lumen 118. Each of the arms 112 may include a contact portion 120 protruding radially inward (i.e., toward an axis of the lumen 118) from a proximal end 122 of a radially inner surface 124 of the arm 112. Each of the arms 112 may also be angled inward toward the longitudinal axis of the lumen 118 such that a distance between the contact portions 120 is substantially the same as or smaller than a diameter of the lumen 118. This permits the contact portions 120 to hold the guidewire 106 along the axis of the lumen 118 proximally beyond the proximal end of the lumen 118. In a preferred embodiment, the device 102 includes two arms 112. However, it will be understood by those of skill in the art that the device 102 may include any number of arms 112 so long as the arms 112 are formed about the lumen 118 with that the contact portions 120 thereof positioned to hold a guidewire 106 received within the lumen 118 on the axis of the lumen 118.

The drilling tool 104, as shown in FIGS. 5-8 may be any device capable of drilling a hole in the bone 108 or reaming an existing hole in the bone 108 by sliding along the guidewire 106 such as, for example, a hollow drill. The drilling tool 104 includes a lumen 130 extending therethrough for accommodating the guidewire 106. The lumen 130 of the drilling tool 104 includes a distal portion 132 sized and shaped to accommodate the device 102 and a proximal portion 134 extending proximally therefrom sized and shaped to accommodate the guidewire 106. The lumen 130 includes a shoulder 136 angled radially outward at a point where the distal portion 132 and the proximal portion 134 meet such that a cross-section of the distal portion 132 distal of the shoulder 136 is larger than a cross-section of the proximal portion 134 proximal of the shoulder 136. A distal end 140 of the drilling tool 104 includes a cutting edge sized and shaped to drill a desired cortical opening with an outer surface 138 of the drilling tool 104 sized shaped accordingly. As would be understood by those skilled in the art, the guidewire 106 may be any standard wire useful for guiding a drilling tool 104 therealong. For example, the guidewire 106 may be a Kirschner wire (k-wire).

According to an exemplary method of use of the system 100, a distal end 126 of the guidewire 106 is inserted into the bone 108 at a desired position and/or angle for the cortical opening. A proximal end 128 of the guidewire 106 is inserted through the lumen 118 at the distal end 114 of the device 102 and the device 102 is slid over the guidewire 106 until the distal end 114 comes into contact with the bone 108. It will be understood by those of skill in the art that the contact portions 120 of the arms 112 hold the guidewire 106 firmly therebetween. Once the device 102 has been slid to the appropriate position, the proximal end 128 of the guidewire 106 is inserted into the lumen 130 of the drilling tool 104 such that the drilling tool 104 is slidable therealong, as shown in FIGS. 5 and 6, in a guiding configuration. In the guiding configuration, the contact portions 120 of the arms 112 hold the guidewire 106 therebetween such that, even when a bending force is exerted on a portion of the drilling tool 104, the drilling tool 104 will not become displaced and will be guided therealong, co-axially with the guidewire 106. Thus, the drilling tool 104 slides co-axially along the guidewire 106 until the distal portion 132 of the drilling tool 104, reaches the bone. Thus, the device 102 acts as a guide for the drilling tool 104 until the distal end 140 reaches the bone 108, ensuring that the cortical opening will not be displaced or improperly drilled/reamed or damaged.

Figures 7, 8:
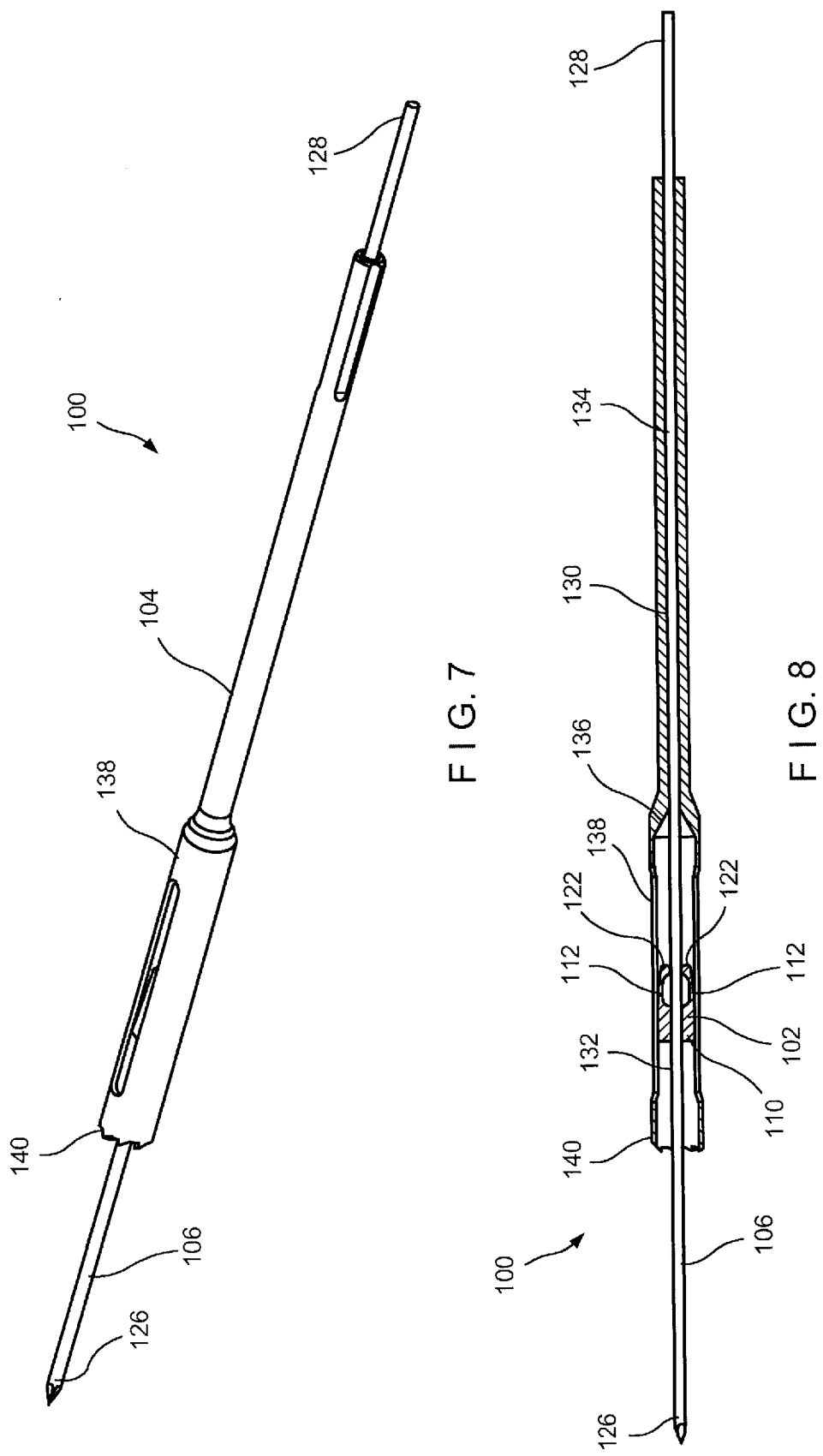
FIG. 7 shows a perspective view of the system of FIG. 1, in a stopping configuration.
FIG. 8 shows a cross-sectional side view of the system of FIG. 7.

During the drilling of the bone, the drilling tool 104 continues to slide distally along the guidewire 106 into the bone 108 such that the device 102 enters the distal portion 132 of the drilling tool 104, as shown in FIGS. 7 and 8, in a stopping configuration. As the drilling tool 104 continues to slide along the guidewire 106 and the device 102, the drilling tool 104 continues to drill through the bone 108. In the stopping configuration, the device 102 slides within the distal portion 132 of the lumen 130 relative to the drilling tool 104 until the device 102 comes into contact with the shoulder 136 of the lumen 130. Thus, in the stopping configuration, the device 102 is within the distal portion 132 of the lumen 118 and acts as a stopper such that once the proximal end 136 of the distal portion 132 abuts the proximal end 122 of the arms 112 of the device 102, the drilling tool 104 may not slide any further distally. Thus, in the stopping configuration, the device 102 stops the drilling tool 104 limiting the drilling of the cortical opening to a predetermined depth. Once the cortical opening has been drilled as desired, the drilling tool 104, the guidewire 106 and the device 102 may simply be removed from the bone 108 such that the intramedullary nail may be inserted into the medullary canal of the bone via the cortical opening.

It will be apparent to those skilled in the art that various modifications and variations may be made in the structure and methodology of the present invention, without departing from the spirit or scope of the invention. Thus, it is intended that the present invention cover the modifications and variations of this invention provided that they come within the scope of the appended claims and their equivalents.

What is claimed is:

1. A device for guiding a drilling tool to form an opening in a bone, comprising:
    a body extending from a distal end to a proximal end, the body including a lumen extending therethrough, the lumen being sized and shaped to slidably accommodate a guidewire therein; and
    a plurality of arms extending therefrom about the lumen with a gripping surface of each arm being spaced radially from an axis of the guide wire lumen by a distance corresponding to a thickness of a guidewire to be received therein, the gripping surfaces gripping the guidewire to maintain a portion thereof extending from the lumen along the axis of the lumen.

2. The device of claim 1, wherein the arms extend proximally from the proximal end of the body.

3. The device of claim 1, wherein the gripping surface of a first one of the arms is formed at a proximal end thereof, the gripping surface extending further radially inward toward the axis of the lumen than portions of the arm extending distally therefrom.

4. The device of claim 1, wherein a length of a first one of the arms is selected so that, when a distal abutting surface thereof contacts a corresponding structure on the drilling tool advanced over a guidewire received within the lumen, a desired depth of drilling has been achieved.

5. The device of claim 1, wherein the arms are angled relative to the axis of the lumen such that proximal ends of each of the arms are closer to the axis of the lumen than are distal ends thereof.

6. The device of claim 1, wherein the body is substantially cylindrical with an outer diameter thereof corresponding to an inner diameter of the drilling tool to be guided thereby.

7. The device of claim 6, wherein the outer diameter of the body is slightly smaller than the inner diameter of the drilling tool to be guided thereby.

8. The device of claim 1, wherein the device is adapted to guide the drilling tool thereover for forming a cortical opening to a medullary canal of a bone.

* * * * *